(12) United States Patent
Robillard et al.

(10) Patent No.: US 8,623,325 B2
(45) Date of Patent: Jan. 7, 2014

(54) AZIDE MODIFIED CHARGE SENSITIVE CHANNEL PROTEINS

(75) Inventors: Marc Stefan Robillard, Eindhoven (NL); George Thomas Robillard, Zuidhorn (NL); Armagan Kocer, Groningen (NL)

(73) Assignee: Koninklijke Philips N.V., Eindhoven (NL)

( * ) Notice: Subject to any disclaimer, the term of this patent is extended or adjusted under 35 U.S.C. 154(b) by 234 days.

(21) Appl. No.: 12/993,130

(22) PCT Filed: May 26, 2009

(86) PCT No.: PCT/IB2009/052195
§ 371 (c)(1),
(2), (4) Date: Nov. 17, 2010

(87) PCT Pub. No.: WO2009/144659
PCT Pub. Date: Dec. 3, 2009

(65) Prior Publication Data
US 2011/0064667 A1    Mar. 17, 2011

(30) Foreign Application Priority Data
May 27, 2008  (EP) .................................... 08156940

(51) Int. Cl.
*A61K 49/00*   (2006.01)
*C07K 14/00*   (2006.01)
*C07C 247/04*  (2006.01)

(52) U.S. Cl.
USPC .......................... 424/1.21; 530/409; 514/150

(58) Field of Classification Search
None
See application file for complete search history.

(56) References Cited

U.S. PATENT DOCUMENTS 5,676,971 A     10/1997  Yoshioka et al.
2006/0204512 A1  9/2006  Krasnoperov et al.
2006/0258587 A1* 11/2006 Kocer et al. .............. 514/12

FOREIGN PATENT DOCUMENTS

| WO | 03000233    A2 | 1/2003  |
| WO | 03084508    A1 | 10/2003 |
| WO | 2005051902  A2 | 6/2005  |
| WO | 2006092722  A1 | 9/2006  |
| WO | 2007039864  A2 | 4/2007  |
| WO | 2007115953  A1 | 10/2007 |

OTHER PUBLICATIONS

Soellner MB, Dickson KA, Nilsson BL, Raines RT. Site-specific protein immobilization by Staudinger ligation. 2003 J. Am. Chem. Soc. 125: 11790-11791.*

Watzke et al. Site-selective protein immobilization by Staudinger ligation. 2006 Angew. Chem. Int. Ed. 45: 1408-1412.*
Kiick et al: "Incorporation of Azides Into Recombinant Proteins for Chemoselective Modification by the Staudinger Ligation"; Proceedings of the National Academy of Sciences, PNAS, Jan. 2002, vol. 99, No. 1, pp. 19-24.
Zhang et al: "P-Azidoiodoacetanilide, A New Short Photocrosslinker That Has Greater Cysteine Specificity Than P-Azidophenacyl Bromide and P-Azidobromoacetanilide"; Biochemical and Biophysical Research Communications, 1995, vol. 217, No. 3, pp. 1177-1184.
Prescher et al: "Chemical Remodelling of Cell Surfaces in Living Animals"; Nature, Aug. 2004, vol. 430. pp. 873-877.
Pivetti et al: "Two Families of Mechanosensitive Channel Proteins"; Microbiology and Molecular Reviews, Mar. 2003, vol. 67, No. 1, pp. 66-85.
Yoshimura et al: "Hydrophilicity of a Single Residue Within Mscl. Correlates With Increased Channel Mechanosensitivity"; Biophysical Journal, Oct. 1999, vol. 77, pp. 1960-1972.
Kocer et al: "A Light-Actuated Nanovalve Derived From a Channel Protein"; Science, Jul. 2005, vol. 309, pp. 755-758.
Roger et al: "Rationally Designed Chemical Modulators Convert a Bacterial Channel Protein Into a pH-Sensory Valve"; Angew. Chem. Int. Ed., 2006, vol. 45. pp. 3126-3130.
Kohn et al: "The Staudinger Ligation—A Gift to Chemical Biology", Angew. Chem. Int. Ed., 2004, vol. 43, pp. 3106-3116.
Shabat et al: "Chemical Adaptor Systems"; Chem. Eur. J. 2004, vol. 10, pp. 2626-2634.
Sukhareva et al: "Constitutive Activation of the Shaker Kv Channel"; J. Gen. Physiol, Nov. 2003, vol. 122, pp. 541-556.
Blume et al: "Liposomes for the Sustained Drug Release In Vivo"; Biochimica Et Biophysica ACTA, 1990, vol. 1029, pp. 91-97.
Klibanov et al: "Amphipathec Polyethyleneglycols Effectively Prolong the Circulation Time of Liposomes"; Federation of European Biochemical Societies (FEBS) 1990, vol. 268, No. 1, pp. 235-237.
Senior et al: "Influence of Surface Hydrophilicity of Liposomes on Their Interaction with Plasma Protein and Clearance from the Circulation: Studies With Poly (Ethylene Glycol)—Coated Vesicles"; Biochimica Et Biophysica ACTA , 1991,vol. 1062, pp. 77-82.
Napoli et al: "Glucose-Oxidase Based Self-Destructing Polymeric Vesicles"; Langmuir, The ACS Journal of Surfaces and Colloids, Apr. 2004, vol. 20, No. 9, pp. 3487-3491.
Napoli et al: "Oxidation-Responsive Polymeric Vesicles": Nature Materials, Mar. 2004, vol. 3, pp. 183-189.
Photos et al: "Polymer Vesicles In Vivo: Correlations With PEG Molecular Weight": Journal of Controlled Release, 2003, vol. 90, pp. 323-334.
Ghoroghchian et al: "Near-Infrared-Emissive Polymersomes: Self-Assembled Soft Matter for In Vivo Optical Imaging"; PNAS, Feb. 2005, vol. 102, No. 8, pp. 922-2927.
Banaszynski et al: "Characterization of the FKBP-Rapamycin-FRB Ternary Complex"; J. Am , Chem. Soc., 2005, vol. 127, pp. 4715-4721.
Van Brakel et al: "A Doxorubicin Prodrug Activated by the Staudinger Reaction", Bioconjugate Chem., 2008, vol. 19, pp. 714-718.
Engberts et al: "Vesicle Forming Synthetic Amphiphiles"; Biochim Biophys ACTA, Dec. 1995, vol. 1241, No. 3, pp. 323-340.

* cited by examiner

*Primary Examiner* — Michael G Hartley
*Assistant Examiner* — Jennifer Lamberski

(57) ABSTRACT

The present invention describes the modification of polypeptides, more particularly channel proteins with a thiol reactive agent so as to introduce an azide group. The present invention further describes vesicles comprising channel proteins modified according to the invention, which upon reaction with a phosphine open up thereby releasing the content of the vesicles. The reagents, polypeptides and vesicles described in the present invention have in vivo and in vitro applications in both drug delivery and imaging.

10 Claims, 7 Drawing Sheets

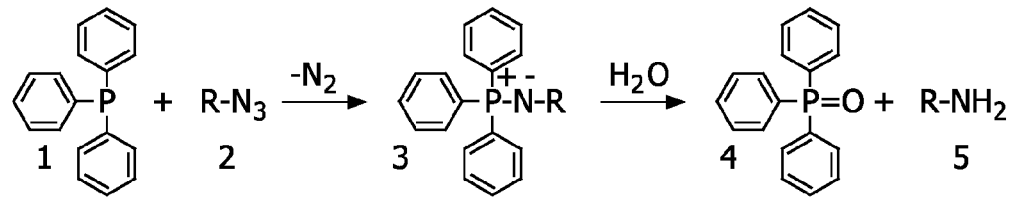
FIG. 2
A. Protein modifying reagents
$$N_3\text{-}Q\text{-}NR_3\text{-}CR_1R_2\text{-}X\text{-}Y\text{-}Z \quad (I)$$
$$N_3\text{-}CR_1R_2\text{-}X\text{-}Y\text{-}Z \quad (II)$$
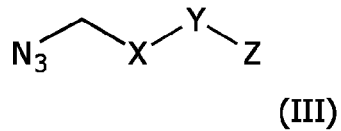
(III)
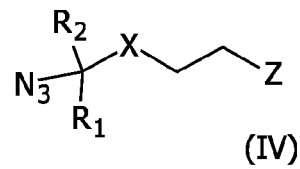
(IV)
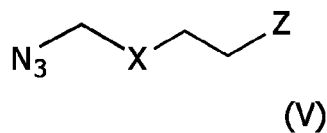
(V)
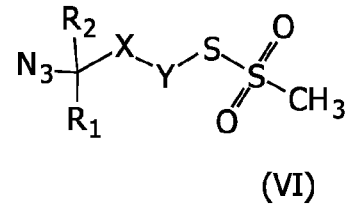
(VI)
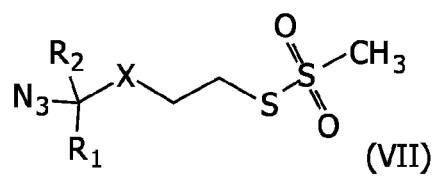
(VII)
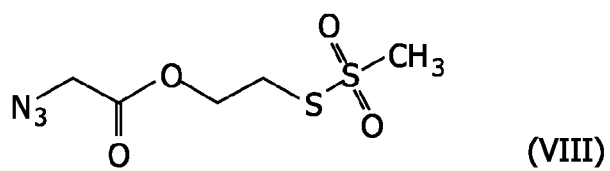
(VIII)
FIG. 3-I

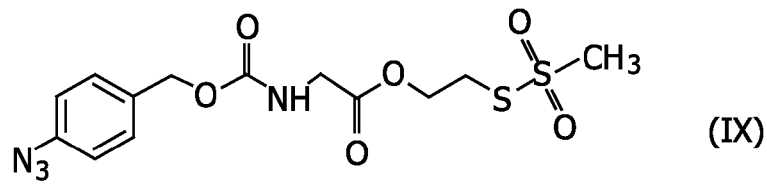
(IX)
A. Protein modifying reagents
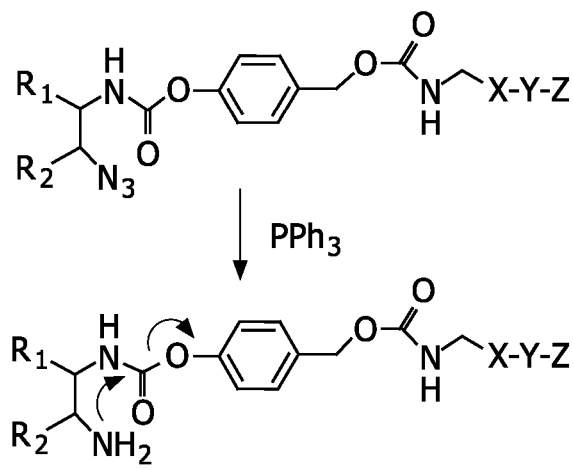
R1, R2=alkane, alkene, aromate, sulfate, part of the same aromate
B. linkers
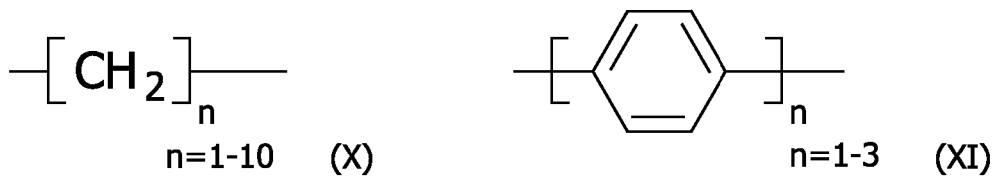
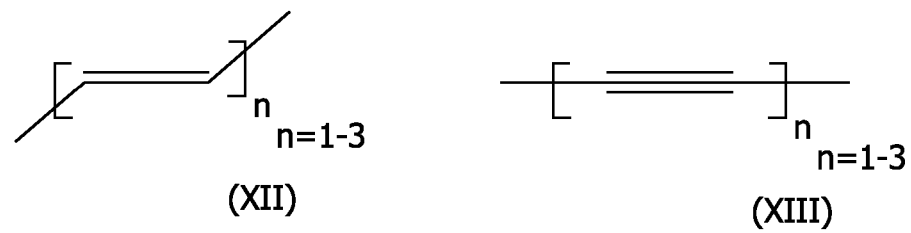
FIG. 3-II

C. thiol reactive groups
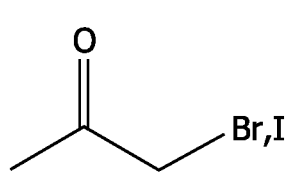 (XIV)
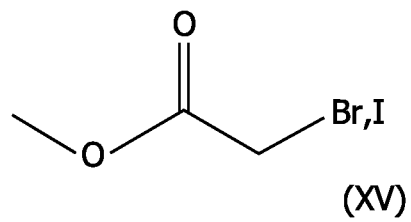 (XV)
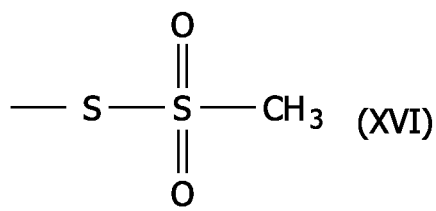 (XVI)
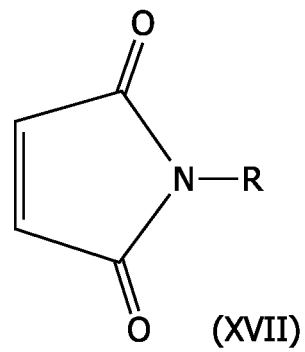 (XVII)
D. modified cysteine side chains
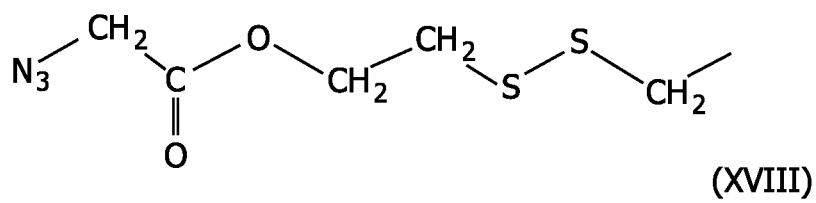
(XVIII)
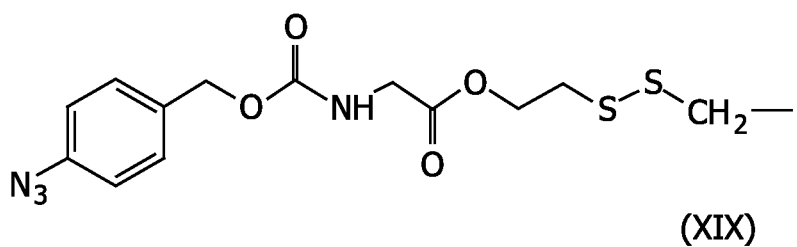
(XIX)
FIG. 3-III

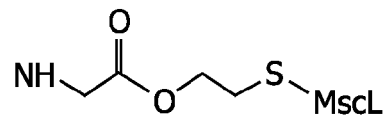
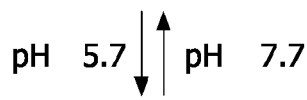
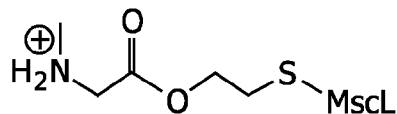
FIG. 4
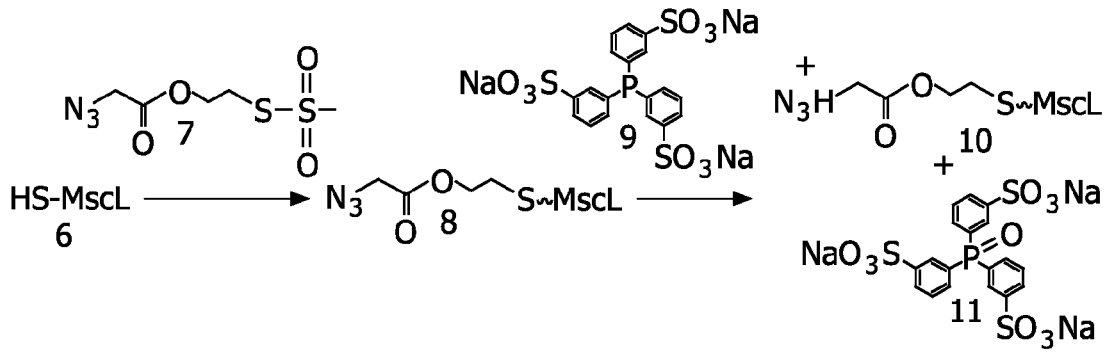
FIG. 5
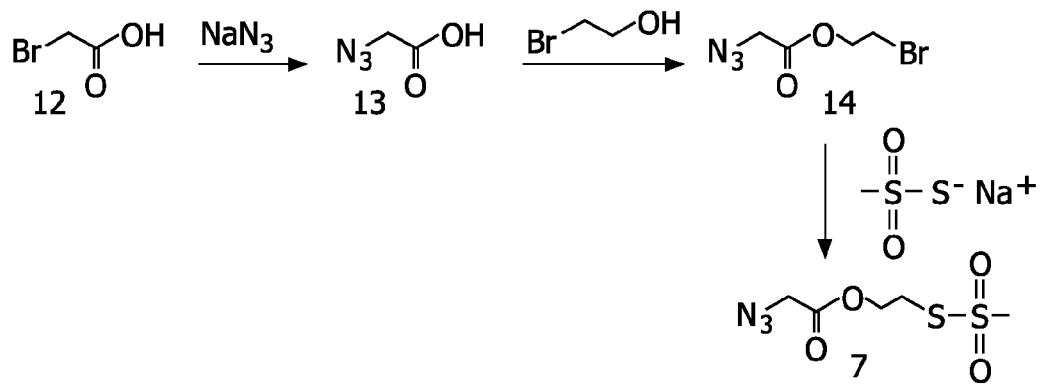
FIG. 6

AZIDE MODIFIED CHARGE SENSITIVE CHANNEL PROTEINS

FIELD OF THE INVENTION

The present invention relates to protein modification, more specifically to the modification of a thiol function and to novel compounds for use in these methods. The present invention further relates to modified channel proteins and their use in vesicles, more particularly lipid vesicles, for drug delivery systems.

BACKGROUND OF THE INVENTION

The goal of drug delivery systems is to increase the efficacy and safety of both new and existing drugs. A number of drug compounds cannot be delivered safely and/or effectively by conventional routes or dosage forms such as oral tablets or injection. Alternative delivery methods can increase safety by sequestering reagents in carriers that reduce systemic exposure and decrease dose-limiting toxicity and side effects, or by providing sustained delivery so that therapeutic levels can be achieved with fewer and smaller doses. New delivery systems can also increase efficacy by several strategies, including:

Increasing stability of the drug;

Increasing the ability of the drug to reach its therapeutic target by prolonging the circulating half-life; and Targeting delivery to the therapeutic site in order to reduce the total circulating dose without diminishing efficacy;

For drugs with a narrow therapeutic index, many of the approaches that reduce toxicity also enhance efficacy thereby increasing the therapeutic window and efficacy of drugs. The most prominent delivery systems used in the clinic are based on liposomes (e.g. Doxil which are liposomes filled with doxorubicin).

There are two liposomal targeting strategies: passive and specific. Passive targeting refers to the preferential accumulation of liposomes in tumours and at sites of infection and inflammation. Small sterically stabilized liposomes extravasate through leaky blood vessels that are formed through tumour angiogenesis or damaged by infection and inflammation. The liposomes accumulate in tumour interstices and at sites of infection and inflammation, where they gradually release their encapsulated drugs. This sequesters potentially toxic agents from susceptible non-target sites such as the brain, liver and heart. The mechanism of liposome accumulation may be a combination of the leakiness of the newly forming or damaged capillaries and enhanced vascular permeation by the coated liposomal particles themselves.

Specific targeting involves the use of antibodies or ligands to tag liposomes so that they bind specifically to cells that express the appropriate cell-surface antigens or ligand receptors, respectively. In principle, liposomes can be targeted to any cell surface structure that can be recognised by a fragment of a specific antibody, or to any receptor for which a small and specific ligand can be produced. Hence, liposomes can be directed to specific classes of T and B lymphocytes or to tumour cells preferentially expressing high levels of specific cell surface proteins. The goals of ligand targeting of liposomes are to concentrate them selectively at the therapeutic site, decrease the required dose by reducing non-specific losses, and reduce systemic exposure to reagents with toxic side effects. There are two caveats, however: 1) The target cells must be accessible; and 2) The reagents must be released from the liposomes efficiently enough to have a clinically significant effect.

One important caveat of liposomal drug delivery is the efficiency of drug release from the liposome at the target location, which determines the clinical effect. This release can be governed by multiple processes and variables. Localisation of passive or active targeted liposomes is usually followed by a relatively lengthy process which can involve an internalisation pathway followed by intracellular processing and drug release or expulsion back to the extracellular domain. Alternatively, these constructs stay in the extracellular domain and are slowly degraded, depending on the specific environment. When liposomes are taken up by cells through endocytosis, the liposome needs to be degraded and the drug has to be able to escape the lysosomal compartment. In this respect it should be noted that endothelial cells do not possess a machinery to degrade liposomes and as a result these constructs are expulsed back to the extracellular environment. Currently the targeting and localisation of liposomes can be controlled by passive or active methods, but there is only an indirect, unpredictable and non-universal control over the subsequent release from these liposomes. The release pathway, the extent of release, the release profile (slow or bolus), and the timing, all depend on the specifics and peculiarities of the target.

To address this issue, liposomal delivery systems capable of near instantaneous release of their content under the influence of redox state, pH or light have been developed.

The technology is based on a well-studied bacterial channel protein "Mechanosensitive channel of large conductance", MscL, from *E. coli*. In its native form the channel creates a large non-selective pore of 3-4 nm in diameter in the membrane and allows the passage of not only ions but also small molecules, peptides and smaller proteins (up to 7 kDa). In nature, MscL opens in response to the tension in the membrane. It has been shown that the hydrophilicity of the $22^{nd}$ amino acid position of MscL affects the mechanosensitivity of the channel up to a point where it starts to open even in the absence of tension (Yoshimura et al. (1999) *Biophys. J.* 77, 1960-1972). Hydrophilic substitutions in this narrow pore constriction area of the channel cause hydration of the pore and weakening of the hydrophobic van der Waals forces responsible for the close packing of the inner membrane helices in the closed state of the channel. The effect is reinforced if charged or bulky groups are introduced because of electrostatic repulsion and steric factors, respectively. This is reflected in the energetics of the gating transitions and leads to the opening of the channel even in the absence of tension.

On the basis of this principle, the MscL protein was re-engineered to site-selectively-incorporate (masked) amine-functionalised molecules. A series of small modulators were designed, synthesised and specifically attached to an engineered Cys at position 22 in MscL. The working principle, depicted in FIG. 1, is that the protein-attached modulators would be charged only in response to a pre-defined stimulation (pH, light, etc) leading to hydration of the hydrophobic constriction zone of the pore and channel opening in the absence of the natural stimulus. The masked reagents possess a nitrophenol moiety, which is removed upon illumination. This affords a free amino moiety which, depending on the pH, can get protonated and trigger the opening of the channel. The ability to control the release of liposome content with reversible channel opening and closing was demonstrated under the influence of UV and visible light, respectively (Kocer et al. (2005) *Science* 309, 755-758) and in response to a decrease in pH using channels modified to respond directly to pH as well as channels engineered (using masked reagents) to respond to pH only after illumination (Kocer et al. (2006) *Angew. Chem. Int. Ed.* 45, 3126-3130). Rationally designed chemical modulators convert a bacterial channel protein into a pH-sensory valve. This methodology is also disclosed in PCT patent applications WO2005051902, WO03084508 and WO03000233.

The activateable liposomal drug delivery systems discussed above allow an increased level of control over drug release from liposomes using light- or pH-mediated release. These mechanisms provide an additional selectivity for a specific local environment (low pH in certain tumours) or localised illumination. However, the drawback of this additional selectivity is that these tools can not be universally applied. Due to the low penetration depth of light, the technology of controlled drug delivery is limited to disorders situated at or near the body surface or in combination with a catheter-light pipe. With respect to the pH-activateable liposomes, many potential targets do not have a pH that is significantly different from surrounding non-target tissue.

Accordingly, there remains a need for drug delivery systems whereby the drug release can be effectively controlled.

SUMMARY OF THE INVENTION

Particular and preferred aspects of the invention are set out in the accompanying independent and dependent claims. Features from the dependent claims may be combined with features of the independent claims and with features of other dependent claims as appropriate and not merely as explicitly set out in the claims.

The present invention provides methods for introducing the phosphine reactive azide reagent of the Staudinger reaction on a thiol group of a peptide or protein, such that it can be used to modify the structural/functional properties of the protein. In particular embodiments of the invention, the Staudinger reaction, a selective chemical and bioorthogonal reaction is used for the in vivo activation of localised drug-filled liposomes and affords superior control over drug release profiles and their therapeutic effect. The application of this technology in drug delivery systems increases the therapeutic window of existing or novel drugs, by providing control over the release from their carriers, facilitating tailored and more effective therapeutic protocols.

One aspect of the invention provides compositions comprising a vesicle, particularly a lipid vesicle, comprising a channel protein or functional fragment thereof, characterised in that the channel protein or fragment thereof comprises, in a side chain of an amino acid of said protein or fragment thereof, a phosphine-reactive azide group.

According to particular embodiments, vesicles are provided wherein a phosphine-reactive azide group is linked to a channel protein or fragment thereof through a sulphur.

According to further embodiments, vesicles are provided wherein the phosphine-reactive azide group is linked to a cysteine in a channel protein or fragment thereof.

In further particular embodiments, vesicles are provided wherein a channel protein, which is a cysteine mutant of a wild-type channel protein is provided with a phosphine-reactive azide group.

In particular embodiments, vesicles are provided comprising a channel protein which is a mechanosensitive channel of large conductance (MscL), more particularly *E. coli* MscL comprising a Gly22Cys mutation, which is provided with a phosphine-reactive azide group.

According to particular embodiments, vesicles are provided with a channel protein comprising a substituted amino acid, the side chain of the amino acid having the structure depicted in formula XVIII:

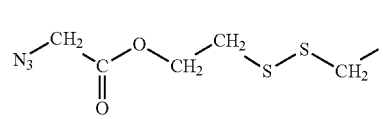

or the structure depicted in formula XIX:

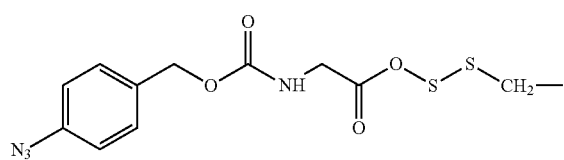

According to further particular embodiments, compositions described herein comprising vesicles as described above further comprise, within the vesicles a bioactive agent. Most particularly, the bioactive agent is a peptide or protein with a length up to about 70 amino acids.

According to further particular embodiments, compositions are provided which further comprise an imaging compound and/or a targeting moiety within the vesicles.

Another aspect of the present invention relates to the above compositions for use as a medicament and/or as an imaging agent.

Accordingly, the present invention provides in vivo methods of controlled drug delivery in a patient based on the use of vesicles such as described herein. More particularly, methods according to particular embodiments comprise the steps of:
administering to the patient a composition comprising:
a vesicle, particularly a lipid vesicle comprising a channel protein or functional fragment thereof, wherein the channel protein or fragment thereof comprises, in a side chain of an amino acid of said protein or fragment thereof, a phosphine-reactive azide group, and
within the vesicle a drug, and
administering a phosphine to the patient.

Similarly, the present invention provides in vivo methods of imaging an organ or tissue in a patient based on the use of vesicles as described herein. More particularly, methods are provided comprising the steps of:
administering a composition comprising:
a vesicle, particularly a lipid vesicle comprising a channel protein or functional fragment thereof, characterised in that the channel protein or fragment thereof comprises, in a side chain of an amino acid of said protein or fragment thereof, a phosphine-reactive azide group; and
comprised within the vesicle, an imaging agent to the patient,
delivering a phosphine to the patient, and
taking an image of the organ or tissue of the patient comprising the imaging agent.

A further aspect of the present invention provides in vitro methods of delivering a compound to a cell comprising the steps of applying a vesicle composition as described above which further comprises said compound to a cell, and applying a phosphine to the cell.

A further aspect of the present invention provides kits comprising vesicle compositions as described herein and a phosphine. In particular embodiments of the methods and kits described herein, the phosphine is trisulfonated thriphenylphosphine.

Yet a further aspect of the present invention provides modified peptides and proteins comprising a phosphine-reactive azide group linked to the side chain of an amino acid of the protein or peptide through a sulphur.

According to particular embodiments, the sulphur to which the phosphine-reactive azide group is linked corresponds to a modified thiol function of a cysteine in the peptide or protein.

According to further embodiments modified peptides and proteins are provided wherein a cysteine side chain, carrying an azide group as described herein, is located in a region of the peptides or proteins which upon introduction of a charge modulates the functionality of the peptide or protein.

According to particular embodiments, modified peptide and proteins carrying a phosphine reactive azide group are provided which are channel protein or a functional fragments thereof.

According to particular embodiments, modified channel proteins are provided which correspond to a mechanosensitive channel of large conductance (MscL), more particularly E. coli MscL, comprising a Gly22Cys mutation.

According to another particular embodiment, the phosphine-reactive group is linked to the amino acid with a side chain having the structure depicted in formula XVIII:

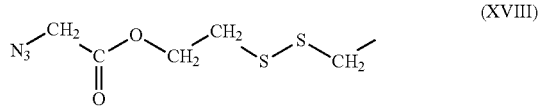

or the structure depicted in formula XIX:

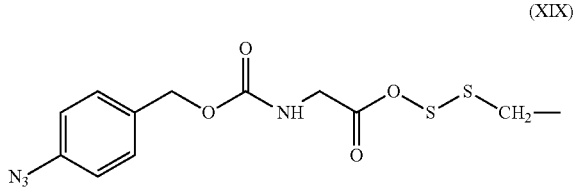 [SMILES: CCSSOC(=O)CNC(=O)OCc1ccc(N=[N+]=[N-])cc1]

A further aspect of the present invention relates to in vitro methods of modifying a phosphine-reactive azide group linked to a peptide or protein through a sulphur into a primary amine group comprising the step of reacting the protein or peptide with a phosphine.

In particular embodiments of this method the phosphine is trisulphonated triphenylphosphine.

Yet another aspect of the present invention provides compounds for modifying thiol groups on a protein or peptide, which compounds have the general formula $N_3$-[Q-$NR_3]_{0-1}$—$CR_1R_2X$—Y—Z (I)

wherein $R_3$ is selected from the group consisting of hydrogen, alkyl, alkene, alkyn, aromate, ether, ester, carbamate, carbonate, oxy, thioester, thioether, amino, hydrazino, sulfur, carbonyl, carboxylic acid, imine, oxygen, amido, sulfate, sulfonate, (oligo)dimethylsiloxane, sulfoxide, phosphates, phosphites and fluorine, wherein Q is an optional self eliminating linker selected from the group consisting of an aromate, alkane, alkene, carbamate, carbonate and combinations thereof, wherein $R_1$ and $R_2$ are independently selected from the group consisting of H, a substituted or unsubstituted $C_1$-$C_6$ alkyl chain, ester, ether, thioester, thioether, amide, amine, imine, alkane, alkene, alkyne, carbamate, carbonate, aromate, sulfate, sulfonate, aminooxy, disulfide, (oligo)dimethylsiloxane, sulfoxide, phosphates, phosphites and fluorine, wherein X is selected from the group consisting of oxygen, sulfur, nitrogen, carbonyl, aromate, alkene, alkyn, ester, ether, thioester, thioether, amide, amine, imine, alkane, carbamate, carbonate, carboxylic acid ester, sulfate, sulfonate, aminooxy, disulfide, (oligo)dimethylsiloxane, sulfoxide, phosphate and phosphite wherein Y is a linker, and wherein Z is a thiol reactive group.

In particular embodiments of the compounds provided herein, $R_1$ and $R_2$ are independently selected from the group consisting of H, and a substituted or unsubstituted alkyl chain with a length of 1, 2, 3 or 4 carbons.

In further particular embodiments of compounds according to the invention having formula (I) described above, X is CO—O.

In further particular embodiments of compounds according to the invention having formula (I) described above, Y is selected from the group consisting of an oxygen, sulfur, nitrogen, carbonyl, aromate, alkene, alkyn, ester, ether, thioester, thioether, amide, amine, imine, alkane, alkene, alkyne, carbamate, carbonate, carboxylic acid ester, aromate, sulfate, sulfonate, aminooxy, disulfide, (oligo)dimethylsiloxane, sulfoxide, phosphate and phosphite Particular embodiments of the above-described compounds are compounds wherein Y corresponds to a structure selected from having one of formulas (X) to (XIII) described herein.

Further particular embodiments of the above compounds are compounds wherein Z is a thiol reactive group selected from the group consisting of an acrylate, maleimide, halogen, disulfide, thioester and thiosulfonate.

Further particular embodiments of the above compounds are compounds wherein Z is a thiol reactive group selected from the formulas (XIV) to (XVII) described herein.

Particular examples of the above modifying compounds are the compounds with formula VIII:

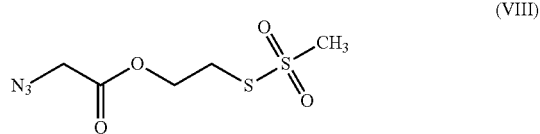

or with formula IX:

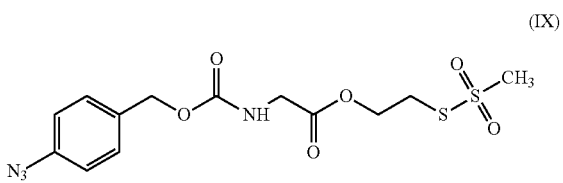 [SMILES: CS(=O)(=O)SCCOC(=O)CNC(=O)OCc1ccc(N=[N+]=[N-])cc1]

Another aspect of the invention relates to the use of the above-described modifying compounds for modifying a thiol group on a protein or peptide for the generation of a protein or peptide comprising an azide function.

Yet another aspect of the present invention relates to methods of preparing a protein or peptide comprising a phosphine-reactive azide group linked to the protein or peptide through a sulphur group, the methods comprising the steps of providing a peptide or protein with a thiol function and contacting the peptide or protein with a thiol modifying compound as described above.

According to particular embodiments of these methods the thiol function is the thiol function of a cysteine in the peptide or protein.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIG. 2 shows a schematic representation of the Staudinger reaction.

FIGS. 3-I to 3-III show exemplary embodiments of modifying reagents according to the present invention.

FIG. 4 shows the pH dependent protonation of primary amines, according to an embodiment of the present invention.

FIG. 5 shows a schematic example of the modification of a channel protein (MscL) and, in a second step, the reaction thereof with phosphine in the Staudinger reaction according to an embodiment of the invention.

FIG. 6 shows a schematic representation of the synthesis of compound (7) according to an embodiment of the invention.

Figure 1:
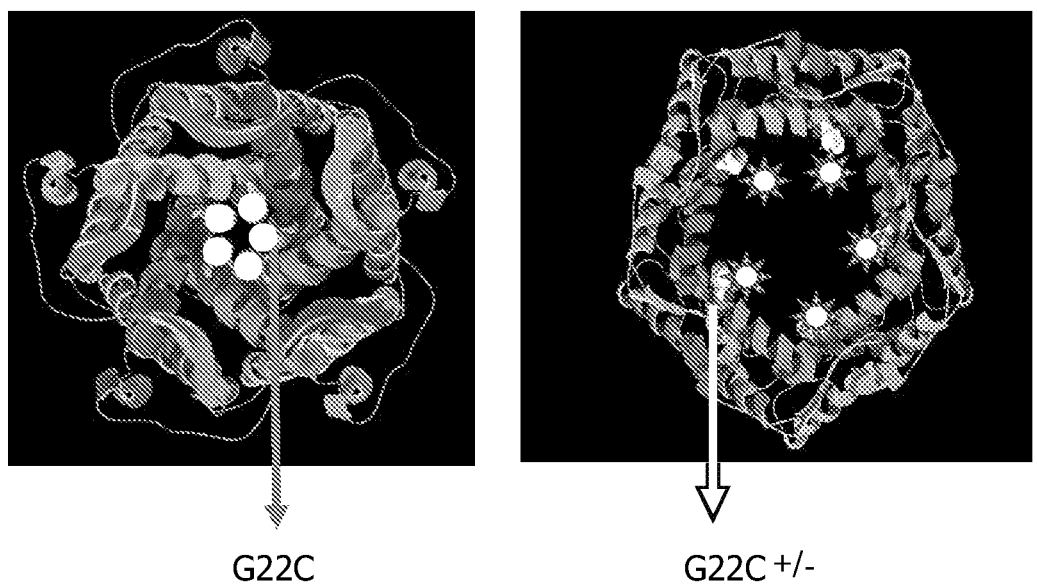
FIG. 1 shows a top view of the *E. coli* MscL channel, which is a homopentamer. The amino acid at position 22 of each of the units is indicated with white circles. The left panel shows the channel in closed confirmation. The right panel shows the channel in open confirmation after stimulation.

In the different Figures, the same reference signs refer to the same or analogous elements.

DETAILED DESCRIPTION OF THE INVENTION

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art.

DEFINITIONS

The term "polypeptide" as used herein relates to any chain of two or more natural or synthetic amino acids linked by a peptide bond and encompasses both the terms peptide and protein. The term "peptide" will be used herein to refer to shorter natural or synthetic polypeptides with a length between 2 and about 50 amino acids, while longer natural or synthetic polypeptides are referred to as "proteins". The term 'modified polypeptide' refers to a polypeptide obtainable by methods according to particular embodiments of the invention whereby a phosphine reactive azide is linked to the polypeptide through a sulphur group, more particularly as a result of the modification of a thiol group of the polypeptide.

The present invention provides reagents and methods for protein modification. More particularly the reagents and methods are of use in the modification of a thiol on a polypeptide, so as to obtain, linked to the sulphur of the thiol, a group that carries an azide which is reactive towards a phosphine in the so-called Staudinger reaction. This is of interest to be able to use the Staudinger reaction in biological processes involving these polypeptides. The Staudinger reaction (represented in FIG. 2) occurs between a phosphine (1) and an azide (2) to produce an aza-ylide (3). In the presence of water, this intermediate hydrolyses spontaneously to yield a primary amine (5) and the corresponding phosphine oxide (4) (Kohn & Breinbauer (2004) *Angew. Chem. Int. Ed.* 43, 3106). The phosphine and the azide react with each other in water at room temperature. Both are abiotic (do not occur in nature) and essentially unreactive toward biomolecules inside or on the surfaces of cells (bioorthogonal). The demands on selectivity imposed by a biological environment preclude the use of most conventional reactions, and thus far only the Staudinger ligation, a strongly related adaptation of the Staudinger reaction, has proven utility in an intracellular environment. The reaction between a triphenylphosphine and an azide has been shown to proceed in vivo (rats) and the two components proved non-toxic in vitro and in vivo (Prescher et al. (2004) *Nature* 430, 873) Moreover, the azide group is small and can be introduced in biological samples without altering the biological size significantly.

One aspect of the present invention provides reagents, which are suitable for modifying a thiol on a polypeptide. Generally stated these reagents comprise a group which is reactive with a thiol function and comprise an azide function which is reactive with a phosphine.

The modifying reagents disclosed herein have, according to particular embodiments, a general structure (I) as disclosed hereafter:

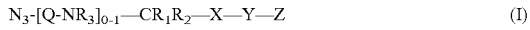

(I)

The [Q-NR$_3$] is optional and Q is a self-eliminating group. Herein, R$_3$ is selected from the group consisting of hydrogen, alkyl, alkene, alkyn, aromate, ether, ester, carbamate, carbonate, oxy, thioester, thioether, amino, hydrazino, sulfur, carbonyl, carboxylic acid, imine, oxygen, amido, sulfate, sulfonate, (oligo)dimethylsiloxane, sulfoxide, phosphates, phosphites and fluorine. Examples of self eliminating groups are aromates, cyclisizing alkanes, alkenes, carbamates, carbonates and combinations thereof. The use of self-eliminating groups in combination with the Staudinger reaction is described in WO2007039864A2 and Shabat et al. (2004) *Chem Eur. J.* 10, 2626-2634.

In the absence of the optional group Q-NR$_3$, the modifying reagents disclosed in the present invention have a general structure as represented by formula II:

$$N_3—CR_1R_2—X—Y—Z \qquad (II)$$

In particular embodiments of the compounds represented by formula (I) and/or (II), R$_1$ and R$_2$ are independently selected from the group consisting of H, a substituted or unsubstituted C$_1$-C$_6$ alkyl chain, ester, ether, thioester, thioether, amide, amine, imine, alkane, alkene, alkyne, carbamate, carbonate, aromate, sulfate, sulfonate, aminooxy, disulfide, (oligo)dimethylsiloxane, sulfoxide, phosphates, phosphites and fluorine. Furthermore, CR$_1$R$_2$ can represent an aromatic ring with or without further substituents. In particular embodiments the nature of the R$_1$ and R$_2$ group is chosen such that the compound after reaction with a phosphine in the Staudinger reaction has a hydrophilic or polar nature.

According to particular embodiments R$_1$ and R$_2$ are independently selected from the group consisting of H and alkyl chains with a length of 1, 2, 3 or 4 carbons.

In further particular embodiments, compounds are provided which are represented by formula (I) and/or (II) described above, wherein X is selected from the group consisting of oxygen, sulfur, nitrogen, carbonyl, aromate, alkene, alkyn, ester, ether, thioester, thioether, amide, amine, imine, alkane, alkene, alkyne, carbamate, carbonate, carboxylic acid ester, aromate, sulfate, sulfonate, aminooxy, disulfide, (oligo) dimethylsiloxane, sulfoxide, phosphate and phosphite. In a particular embodiment, X comprises a carbonyl group (e.g. the carboxylic acid ester CO—O) or consists of a carbonyl group.

In further particular embodiments of the compounds represented by formula (I) and/or (II) described above, Y is a linker selected from the group consisting of oxygen, sulfur, nitrogen, carbonyl, aromate, alkene, alkyn, ester, ether, thioester, thioether, amide, amine, imine, alkane, alkene, alkyne, carbamate, carbonate, carboxylic acid ester, aromate, sulfate, sulfonate, aminooxy, disulfide, (oligo)dimethylsiloxane, sulfoxide, phosphate and phosphite.

Examples of linkers are depicted in formulas (X) to (XIII) in panel B of FIG. 3.

In further particular embodiments of the compounds represented by formula (I) and/or (II) described herein, Z is a thiol reactive group selected from an acrylate such as maleimide, halogen (e.g. Br or I), disulfide, thioester and a thiosulfonate Examples of thiol reactive groups are depicted in formulas (XIV) to (XVII) in panel C of FIG. 3.

In particular embodiments of the compounds of the invention corresponding to formula I and/or II described above, R$_1$ and R$_2$ are H.

In further particular embodiments Y is —CH$_2$—CH$_2$—.
In further particular embodiments X is CO—O.
In further particular embodiments Z is —S—SO$_2$—CH$_3$.
In further particular embodiments Q is —C$_6$H$_4$—CH$_2$—O—CO—.

Formulas of exemplary embodiments of modifying compounds of the present invention are disclosed in FIG. 3 (III to IX of Panel A). Particular embodiments of the modifying reagents of the present invention are the compounds represented by formula (VII) and (XVII), depicted hereafter:

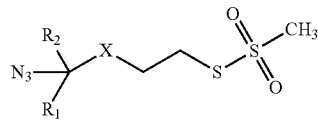

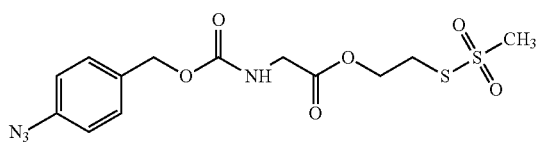

A further particular embodiments is represented by a compound with formula VIII, also designated as MA or compound (7) in the Examples section herein. The preparation of this compound is described in detail in the Examples section.

One aspect of the present invention accordingly relates to the use of the above-described modifying compounds or reagents for the modification of polypeptides for the generation of polypeptides comprising an azide function.

The nature of the polypeptide used for modification in methods according to the present invention is not critical. The polypeptide can be of any length. Typically, the polypeptide has a length of between 25 and 100 amino acids, more typically, less than 70 amino acids. The polypeptide can be isolated from a natural source, can be a recombinant protein or can be a synthetic protein produced by chemical peptide synthesis. The polypeptide can correspond to a naturally occurring wild-type polypeptide or can contain one or more mutations. These mutations can correspond to naturally occurring mutations or can be mutations not encountered in nature and introduced by recombinant technology or during chemical peptide synthesis. The polypeptide can be truncated at the N- or C-terminus or can contain an additional polypeptide sequence in the form of a fusion protein for e.g. purification, affinity or targeting purposes.

More particularly, the present invention provides methods of preparing a modified polypeptide comprising a phosphine-reactive azide group by reacting the polypeptide of interest with the modifying compounds of the invention. More particularly, the methods comprise the steps of providing a polypeptide with a thiol function (e.g. a cysteine side-chain), and contacting the polypeptide with a thiol-reactive reagent according to the invention as described above.

The polypeptides used in the methods of the present invention may comprise a cysteine residue located in an appropriate position in the wild-type protein, and may thus be ready for modification according to methods of the present invention. In these embodiments, the thiol of the side chain of the cysteine amino acid present within the polypeptide is reacted with the thiol-reactive agent. Alternatively, where the polypeptide does not naturally comprise a cysteine in the appropriate position, a cysteine can be introduced by recombinant technology or can be introduced during peptide synthesis.

In further embodiments of the methods of the invention a thiol function is incorporated in the polypeptide of interest via modification of an NH$_2$ group (Lys, N-terminus), a COOH group (Asp, Glu, C-terminus) or an imidazole group (His) using protein modification reagents such as available from e.g. Pierce (Rockville, Ill.).

In further embodiments, a thiol function is incorporated into the polypeptide via peptide synthesis using less frequent natural amino acids such as for example homocysteine or mercaptovaline or using synthetically prepared non-naturally occurring amino acids with a thiol function.

In particular embodiments of methods of the invention, in order to ensure that the reaction is optimal, the thiol of polypeptide is preserved from oxidation or is reduced prior to the reaction with the thiol-reactive reagent. In particular embodiments of methods of the invention, the thiol-comprising polypeptide is reacted with the compounds having formula VIII or IX described herein.

In these methods, the modifying reagent reacts with the reduced thiol group of the polypeptide side chain such that the reagent including the phosphine reactive group is linked onto the sulphur of the thiol group.

In particular embodiments, where the thiol group of interest in the modification methods of the present invention is the side chain of a Cysteine ($SH-CH_2-$) and the thiol-reactive reagent is compound (VIII) as described herein, the resulting side chain of the polypeptide has the structure depicted in formula XVIII:

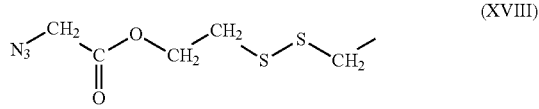

(XVIII)

Similarly, in further particular embodiments, where a cysteine side chain of a protein or polypeptide is modified with compound (IX) as described herein, the cysteine side chain of the resulting modified polypeptide accordingly has the structure depicted in formula XIX:

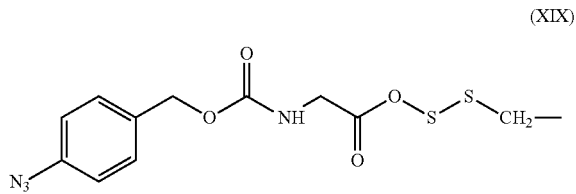 [SMILES: CCSSOC(=O)CNC(=O)OCc1ccc(N=[N+]=[N-])cc1]

(XIX)

Modified polypeptides obtained or obtainable using modification methods described hereinabove comprise an azide linked to the polypeptide via a sulphur. These polypeptides are thus reagents suitable for use in the Staudinger reaction, in in vivo or in vitro conditions, wherein the azide group is reacted with a phosphine, such as trisulfonated triphenyl phosphines.

According to particular embodiments of the modification methods of the present invention, the polypeptide is a channel protein and modification methods of the present invention are used to introduce into the polypeptide a group with a manipulateable charge. More particularly, the polypeptide is a Large-conductance mechanosensitive channel polypeptide or MscL polypeptide, of which the structure/function is charge sensitive. Introducing a manipulateable charge onto an MscL polypeptide makes it possible to manipulate the structure/function of the MscL, i.e. the opening or closing of the channel. The modification of an MscL on cysteine with compound with formula VIII and the subsequent generation of a primary amine in the Staudinger reaction is shown in FIG. 5.

When a polypeptide with a modified thiol with the structure depicted in formula IX described herein, participates in the Staudinger reaction, the azide is reduced to an amine, whereafter its lone pair electrons delocalise into the aromatic ring. This causes the release of a quinone-methide structure, and of carbon dioxide, resulting in a primary amine.

Accordingly, methods of the present invention are of particular interest in the generation of modified polypeptides, which as a result of the introduction of a phosphine reactive azide group on a side chain of the polypeptide can be used in the Staudinger reaction, whereby further to contacting the protein with phosphine, the function of the polypeptide is modified.

Other applications wherein the introduction of a charge in a protein is of interest include a change in structure ($\alpha-\beta$), a change in dipole moment of a helix due to charge at the N- or C-terminus, an alteration of the reactivity of catalytic groups and a change in substrate specificity upon modification of amino acid in the binding site of a protein.

Yet another aspect of the present invention relates to polypeptides comprising a phosphine reactive azide group which is linked to the polypeptide through a sulphur. In particular embodiments, the polypeptides of the present invention are the result of the modification of a thiol side chain (e.g. a cysteine). Most particularly, the modified polypeptides of the invention are obtainable by methods disclosed hereinabove, i.e. by contacting a polypeptide comprising a thiol with a thiol-reactive agent.

The azide group in the modified polypeptides of the present invention carries no charge. Upon reaction with a phosphine in the Staudinger reaction, the azide group is converted into a primary amine, which is protonated at a pH value below its $pK_a$ (7.75), as illustrated in FIG. 4. In particular embodiments, of the present invention the modified polypeptides are polypeptides wherein the introduction of a charge changes the function of the polypeptide.

Particular embodiments of the modified polypeptides of the present invention are channel proteins or functional fragments thereof. Channel proteins are proteins which form channels in membrane structures which channels allow the selective passage of certain molecules and compounds. Fragments of these channel proteins, i.e. truncated at N- and/or C-terminus can maintain the channel protein function of allowing selective passage.

In a more particular embodiment the present invention provides modified large-conductance mechanosensitive channel proteins (MscL). Members of the MscL family show considerable variation in amino acid sequence identity over their complete protein sequences (up to 60%) but all have the conserved sequence motif of Protein Family 01741 [Large-conductance mechanosensitive channel, MscL family]. Particular examples are E. coli MscL [Genbank Accession AAA58088] or L. lactis MscL [Genbank Accession NP_268258].

MscL proteins do not naturally comprise cysteines or thiol side chains. However, different amino acids in MscL proteins can be modified into cysteine for the purposes of the present invention, i.e. introducing a manipulateable charge which affects the conformation of the protein and thus the opening/closing of the channel. These amino acids are located in the regions corresponding to amino acids 1 to 14, 15-45, 46-75 and 76-100 of E. coli. MscL.

In a particular embodiment of the present invention, the modified channel protein is E. coli MscL with the mutation Gly22Cys, L. lactis MscL with the mutation Gly20Cys or another protein of the MscL family mutated at the amino acid corresponding to Gly22 of E. coli MscL comprising a phosphine reactive azide group. It has been demonstrated that modification of this residue into a charged derivative results in the opening of the protein (Yoshimura et al., 1999, cited above).

In further particular embodiments, the modified polypeptide corresponds to the *E. coli* MscL with the double mutation Gly22Cys, Val23Cys or another MscL protein with this double cysteine mutation at the corresponding amino acids comprising a phosphine reactive azide group.

In particular embodiments, the invention provides modified MscLs which, in addition to the phosphine reactive azide group, comprise genetically engineered changes in the outside loop, such as receptor recognising domains (e.g. RGD) or antigen binding parts of an antibody to that loop to obtain target binding of the MscL to a particular tissue organ or cell type.

In yet other embodiments the modified channel protein is a Shaker $K^+$ potassium channel protein comprising a phosphine reactive azide group. Sukhareva et al. (2004) in *J. Gen. Physiol.* 122, 541-566, disclose that the introduction of a charged amino acid at position 475 in Shaker H4 results in the opening of the channel. Accordingly, a particular embodiment of a modified channel protein according to the invention is a Shaker protein comprising a phosphine reactive azide group linked to a thiol side chain. More particularly, the Shaker protein is a protein comprising mutation Pro475Cys in Shaker H4 (Accession P08510) or equivalent positions in proteins of the Shaker family such as Pro406Cys in Kv2.1, Gly229Cys in KvAP, Ala108Cys in KcsA, Glu92Cys in MthK, and Gly143Cys in KirBac.

Channel proteins modified in accordance with the present invention find their application e.g. in the controlled delivery of biological agents and/or imaging compounds. Accordingly, yet another aspect of the present invention therefore relates to a vesicle, particularly a lipid vesicle, comprising a channel protein or functional fragment thereof, wherein the channel protein or fragment thereof is a modified channel protein or fragment comprising a phosphine-reactive azide group as described above. Furthermore the invention provides compositions comprising the vesicles of the invention. Typically, the vesicles are provided suspended in a solution which is typically a physiologically benign buffer.

Depending on the application, the vesicles of the invention can contain a bioactive agent or an imaging compound or both, or another molecule which is of interest.

The compositions and methods making use of the vesicles and/or compositions described herein are particularly suitable for the delivery of small hydrophilic molecules. These can be released from liposomes upon opening of channel proteins comprised within the liposome membrane. Loading of the lipid vesicle can be accomplished in many ways as long as the small molecules are dissolved in a hydrophilic solvent, which is separated from the surrounding hydrophilic solvent by a lipid bilayer.

Negatively charged lipid vesicles are very quickly removed from the blood stream by the Mononuclear Phagocytic System (MPS) in the liver and the spleen. Lipid vesicles that consist of positively and/or neutrally charged lipids are more resistant to uptake by cells of the MPS, exhibit a longer half-life in the bloodstream and have improved targeting to non-MPS cells. Accordingly, in a particular embodiment of the present invention the exterior lipid part of the lipid vesicle provided in the compositions of the invention preferably consists predominantly of positively and/or neutrally charged lipids. The size, shape and composition are parameters which define whether a vesicle will be recognised or not by the reticuloendothelial system. The covering of liposomes with the synthetic polymere polyethyleneglycol (PEG), for example, significantly increases the liposomal half life in the blood (Blume et al. (1990) *Biochim. Biophys Acta* 1029, 91-97; Klibanov et al. (1990) *FEBS Lett* 268, 235-237; Senior et al. (1991) *Biochim. Biophys Acta* 1062, 77-82). Accordingly, in a particular embodiment of the present invention the exterior lipid part of the lipid vesicle provided in the compositions of the invention is functionalised with a polymeric PEG.

A lipid vesicle can comprise lipids but may also comprise other molecules. Glycolipids or lipids modified in other ways that maintain the classical bipolarity are also considered 'lipids' in the context of the present invention.

In a particular embodiment of the invention the lipid vesicle is a liposome, more particularly a long circulating liposome. Liposomes are typically spherical lipid bilayers from 50 nm to 1000 nm in diameter. Long circulating liposomes are typically small (150 nm or smaller), neutral and have a specific composition (cholesterol-containing with either phosphatidylcholine and PEG or sphingomyelin etc).

Liposomes are known as convenient delivery vehicles for biologically active molecules. Methods to incorporate channel proteins in liposomes are described in detail e.g. in WO2005/051902.

In particular embodiments, non-lipid vesicles are used as vesicles. Such vesicles, suitable for drug delivery are known to the skilled person (Engberts & Hoekstra (1995) *Biochim Biophys Acta.* 1241, 323-40). Examples of such non-lipid vesicles are for example synthetic amphiphilic block copolymers ("polymersomes") of ethylene glycol and propylene sulfide (Napoli et al. (2004) *Langmuir* 20, 3487-3891; Napoli (2004) *Nat Mater.* 3, 183-189; Photos et al. (2003) *J Control Release.* 90, 323-334) and amphiphilic diblock copolymers (Ghoroghchian (2005) *Proc Natl Acad Sci USA.* 102, 2922-2927).

In particular embodiments of the invention, the vesicles or liposomes comprise (mutant) MscL proteins modified to comprise a phosphine-reactive azide group according to the present invention. In more particular embodiments, the MscL protein is an *E. coli* MscL with mutation Gly22Cys. More particularly the modified MscL protein has been obtained by contacting the protein with the reagent with formula VIII as described herein.

Considering that proteins such as MscL are foreign proteins it is conceivable that upon repeated administration the host mounts an immune response. To allow at least a limited evasion of the immune system of the host so-called masking groups can be attached to the outside of the lipid vesicle. Preferably, such masking groups comprise PEG.

The vesicles and compositions of the present invention are particularly suitable for the delivery of hydrophilic small molecules that are small enough to pass through the pore of a channel protein. Typically these small molecule have a diameter of no more than 60 Ångstrom, more particularly no more than 50 Ångstrom and more particularly no more than 40 Å. Example hereof are peptides and also proteins with a length of about 60 to 70 amino acids (i.e. proteins with a Mr up to about 7000). Peptides typically have very poor pharmacodynamic properties when injected into the bloodstream. Within a vesicle it is possible to significantly increase the half-life of peptides in the circulation. Moreover, by enabling controlled release of a small molecule with a vesicle of the invention it is also possible to have locally a relatively high bio-availability of the peptide, whereas systemically the bio-availability is low or even absent. This also allows for the therapeutic use of molecules that are otherwise too toxic when bio-available systemically.

Examples of hydrophilic small molecules that are envisaged to be provided in the vesicles of the present invention include, but are not limited to, peptides and proteins that modulate the immune response such as interleukins; potent inhibitors of protein synthesis in human cells such as *Diphteria* toxin (fragment); activators of immune system for macrophage-mediated destruction of tumour cells such as muramyl dipeptide; drugs for the treatment of lung fibrosis such as Cis-4-hydroxyproline; compounds for cancer treatment such as Cisplatin and derivatives thereof, cytosine arabinose, carboplatin, methotrexate, 1-S-D-arabino-furanyl-cytosine (ara-C), 5-fluoro-uracil, floxuridine, and gemcitabine; antibacterial agents such as phosphonopeptides; activator of prodrugs such as -ss-Glucuronidase for the activation of e.g. epirubicin-glucuronide; cytostatic drugs such as (doxorubicin, ciplatin etc.); small therapeutic proteins and peptides such as insulin, growth factors and chemokines.

In particular embodiments, the vesicles of the present invention further comprise, in addition to one or more modified channel proteins, one or more non-channel molecules. Such non-channel molecules include one or more targeting moieties. Typically, a targeting moiety is an antibody or a protein with affinity for a certain cell type or tissue. Other targeting moieties, which can be incorporated in the wall of a vesicle according to the invention, are vitamins and carbohydrates.

Vesicles, particularly lipid vesicles, comprising channel proteins modified according to the present invention, have important applications in the medical field. Accordingly, yet another aspect of the present invention relates to the use of the vesicles comprising the modified channel proteins according to the present invention as a delivery system for a drug and/or an imaging agent. Accordingly, the present invention provides vesicle compositions comprising one or more bioactive agents and/or one or more imaging compounds (or other compounds useful in the context of therapy or diagnosis) for use as a medicament and/or an imaging agent.

This aspect of the present invention provides in vivo methods of controlled drug delivery in a patient comprising the steps of (a) administering a composition comprising a vesicle with channel proteins modified with an azide group and comprising a drug to the patient, and (b) administering a phosphine to the patient in order to open the channel proteins in the vesicles and thus allow release of the drug from the vesicle.

This aspect of the present invention further provides in vivo methods of imaging an organ or tissue in a patient comprising the steps of (a) administering a composition comprising a vesicle comprising one or more channel proteins modified with an azide group and comprising an imaging agent to the patient, and (b) administering a phosphine to the patient in order to allow release of the imaging agent from the vesicle. Hereafter an image is taken of the organ or tissue of the patient comprising the imaging agent.

Accordingly, the methods of the present invention comprise the step of administering a phosphine. In particular embodiments the phosphine is trisulfonated triphenylphosphine.

Other aspects of the present invention provide in vitro applications of the vesicles comprising the modified channel proteins described herein. One aspect of the present invention relates to an in vitro method of delivering a compound to a cell comprising the steps of contacting a vesicle having one or more channel proteins modified with an azide group comprising the compound of interest with the cell and contacting the cell with a phosphine in order to allow the channel protein to be opened and to release the compound from the vesicle.

In the context of the in vivo or in vitro applications described above the present invention further provides kits for performing these methods comprising a vesicle comprising a modified channel protein such as described herein and a phosphine. In particular embodiments the phosphine is trisulfonated triphenylphosphine.

The methods and tools of the present invention provide an advanced level of control over liposomal release properties by introduction of a two-step triggering mechanism, which will be generally applicable to any part of the body.

The use of a masked reagent and the response to (physiological) pH as the primary triggering mechanism is retained. However, the activation mechanism of the masked reagent is changed from illumination as described in the prior art to mild reduction via the selective chemical, bioorthogonal and biocompatible Staudinger reaction.

Other arrangements of the systems and methods embodying the invention will be obvious for those skilled in the art. It is to be understood that although preferred embodiments, specific constructions and configurations, as well as materials, have been discussed herein for devices according to the present invention, various changes or modifications in form and detail may be made without departing from the scope and spirit of this invention.

EXAMPLES

Example 1

Preparation of the Thiol Reactive Reagent of Formula (VIII)

Compound 13 was prepared following a published procedure disclosed in Banaszynski et al. (2005) *J. Am. Chem. Soc.* 127(13), 4715-4721.

Compound 14 was prepared by adding bromoethanol (7.3 mL, 102 mmol) to azide 13 (1.03 gram, 10.2 mmol). The pink solution was cooled to 0° C. and thionylchloride (0.94 ml, 13 mmol) was added dropwise over a period of 10 minutes, keeping the reaction mixture below 10° C. The reaction mixture was stirred at RT for 1 h and subsequently toluene (150 ml) was added and the solution was evaporated. To the resulting light brown liquid dichloromethane (100 ml) was added and the solution was washed with water (3×100 ml), brine, dried over $MgSO_4$, filtered and evaporated. Column chromatography (silica gel, dichloromethane) afforded 14 as a colourless liquid (1.60 gram, 7.7 mmol, 75%). $^1H$ NMR (300 MHz, $CDCl_3$) δ 4.52 (t, 2H, J=6.0 Hz), 3.95 (s, 2H), 3.55 (t, 2H, J=6.0 Hz). $^{13}C$ NMR (75 MHz, $CDCl_3$) δ 155.9, 65.5, 65.3, 50.6, 28.5. GCMS: m/z: 208 $[M+H]^+$ The Azide 7 was obtained by adding sodium MTS (1.14 gram, 8.5 mmol) to a solution of 14 (1.60 gram, 7.7 mmol) in DMF (8 ml). The mixture was stirred at 70° C. for 5 h. A white precipitate formed, which was filtered off, and the yellow solution was evaporated, affording a yellow liquid mixed with a white solid. Addition of chloroform to the mixture resulted in more white precipitate which was again filtered off. The yellow solution was evaporated and the resulting liquid purified by column chromatography (silica gel, chloroform/ethylacetate, 9/1) yielding 7 as a slightly tanned liquid (1.18 gram, 4.9 mmol, 64%) $^1H$ NMR (300 MHz, $CDCl_3$) δ 4.52 (t, 2H, J=6.1 Hz), 3.94 (s, 2H), 3.45 (t, 2H, J=6.1 Hz), 3.38 (s, 3H). $^{13}C$ NMR (75 MHz, $CDCl_3$) δ 155.9, 64.0, 51.4, 50.6, 35.1. GCMS: m/z: 240 $[M+H]^-$, 257 $[M+NH_4]^+$. IR: 2130 $cm^{-1}$ (azide). Anal. Calcd for $C_5H_9N_3O_4S_2$: C, 25.10; H, 3.79; N, 17.56; S, 26.80; O, 26.80. Found: C, 25.3; H, 3.8; N, 17.3; S, 27.1, O, 26.8.

The synthesis of this compound is shown in FIG. 6.

Example 2

Labelling of MscL with a Thiol Reactive Azide

The *E. coli* channel protein MscL Gly22Cys was labelled with azide 7 (abbreviated as MA) during its isolation. Details on the recombinant expression of MscL are described in detail in WO2005051902. Recombinant His-tagged MscL was overexpressed in a bacterial host. The membrane of the host containing recombinant MscL was solubilized in detergent containing buffer and it is applied to a Ni-NTA affinity column. MA (7) dissolved in DMSO is added to the bound protein (theoretical final concentration 100 mM) and incubated for 30 min at RT. Since the channel is a homopentamer, the modification builds in 5 azide moieties, which face each other in the hydrophobic pore of the MscL channel. Unreacted MA is washed from the column and the azide labelled His-tagged protein is eluted with a Histidine gradient. MscL protein modified with the thiol reactive azide (7) is abbreviated as MsCl-MA.

Example 3

Reconstitution of MscL-MA into Liposomes Containing Calcein

MscL-MA was reconstituted into synthetic liposomes composed of azolectin by using a detergent mediated reconstitution method. The incorporation of channels protein in lipid vesicles is describe in detail in WO2005051902 This procedure was performed in the presence of calcein, a self-quenching fluorescent dye. At high local concentrations inside the liposomes, the fluorescence of calcein is low. Release of calcein from liposomes results in dilution of the dye and consequently in a large increase in fluorescence intensity. The labelling and reconstitution was validated by using unlabeled MscL instead of MscL-MA.

Example 4

Release from Azide Labelled MscL Activity/Function

The activity of azide labeled Gly22Cys MscL in the liposome was verified with triphenylphosphine (Trisodium triphenylphosphine-3,3',3"-trisulfonate) at pH 7.2-7.5 at 37° C.

A control experiment was performed using vesicles with unlabelled Gly22Cys MscL and the channel activator MTSET, which is a charged and cysteine-reactive molecule. Addition of MTSET to the calcein-filled and unmodified MscL-containing liposomes resulted in calcein release (FIG. T, top panel).

Figure 7A:
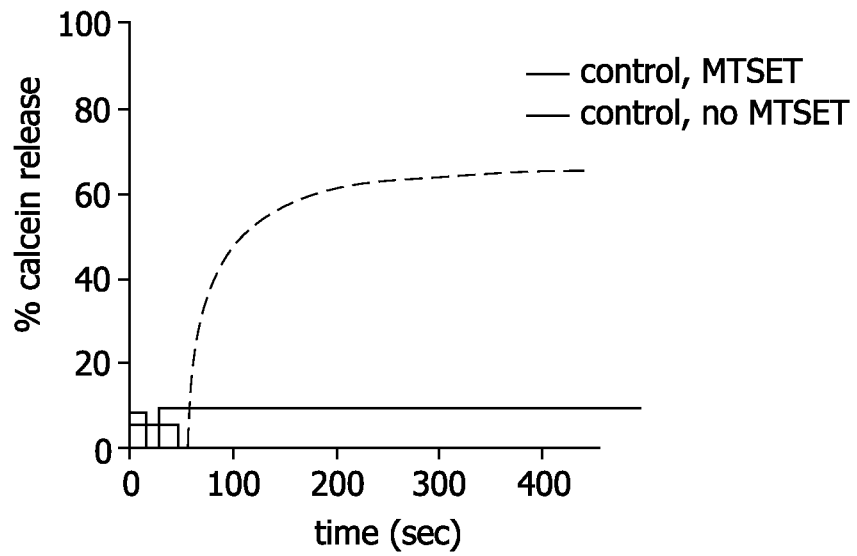
FIG. 7A shows a comparative example wherein the influence of MTSET on the release of calcein from vesicles form MscL is measured. (baseline: unmodified MscL; hyperbolic curve MscL modified with MTSET).
Figure 7B:
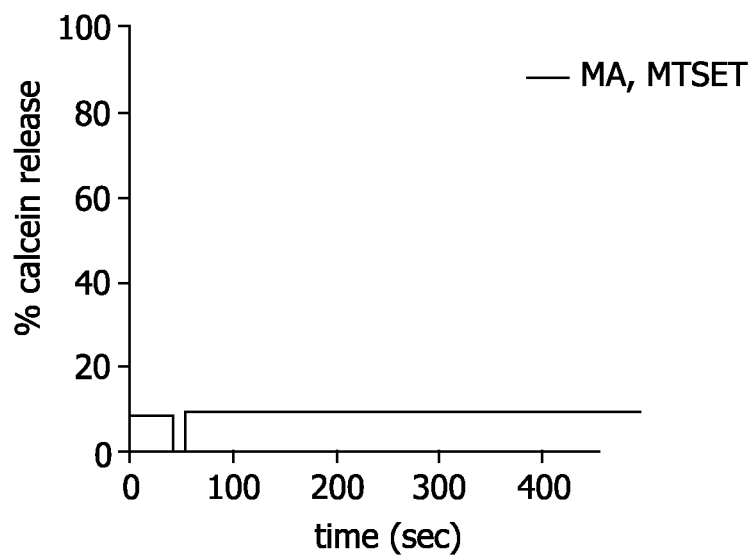
FIG. 7B shows a control experiment wherein the influence of MTSET on the release of calcein from vesicles with an azide-modified MscL is measured. As the azide-modified MscL comprises azides on all cysteines, MTSET could not activate the modified MscL.

Another control experiment was performed to demonstrate that all cysteine residues in MscL-MA were effectively labelled with MA. MscL-MA has a closed conformation. Calcein can not leave from a vesicle via this closed MscL-MA. To these vesicles MTSET was added. Unlabelled cysteine residues, if present, will react with MTSET and introduce a charge in the channel protein resulting in the opening of the channel and release of fluorescent label. Such residual activation was not observed, showing that a quantitative MA labelling of all cysteines in MscL was obtained (FIG. 7, bottom panel). Consequently, MTSET could not activate MscL.

In the experimental setting calcein-filled vesicles with MscL-MA are treated with triphenylphosphine at pH 6.0.

Control experiments are performed using the same calcein filled vesicles with MscL, which is not modified with MA and wherein these unmodified vesicles are treated with triphenylphosphine.

Figure 8:
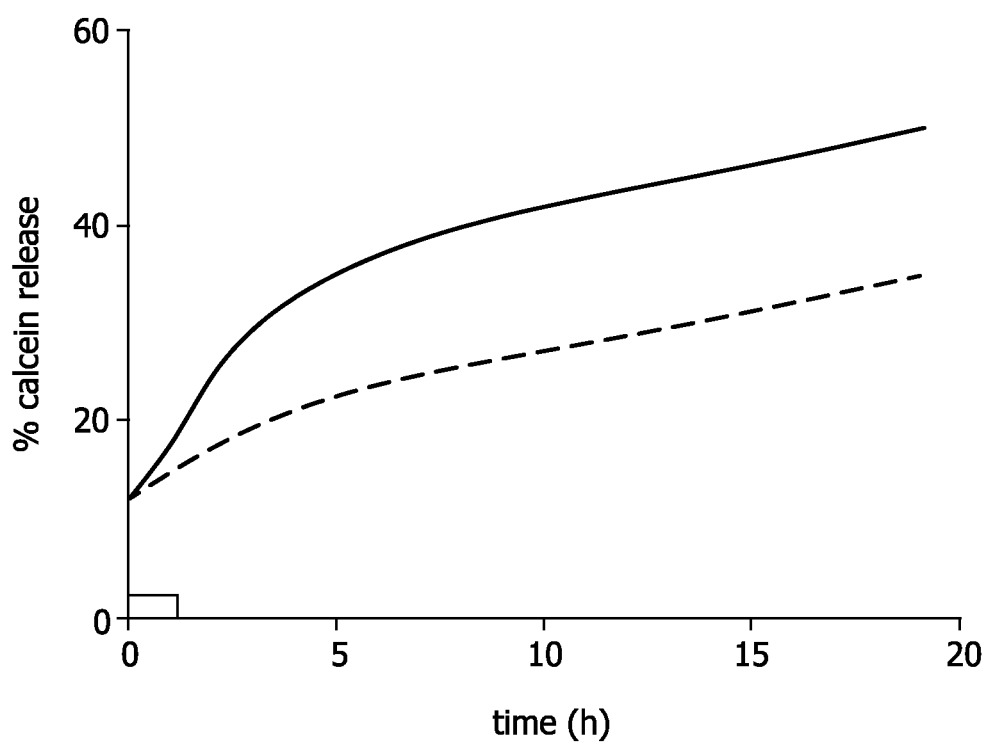
FIG. 8 shows the release of calcein from vesicles with azide-modified-MscL. Solid line: azide modified MscL at pH 6; dotted line: unmodified MscL at pH 6)

After incubation of MscL-MA with phosphine (solid line in FIG. 8) vesicles showed a higher release as compared to the control (MscL without phosphine, dotted line in FIG. 8).

Upon reaction of the liposome with triphenylphosphine (9) the primary amine 10 is formed. The $pK_a$ of this amine is 7.75 and will protonate at physiological pH, This protonation in turn results in the opening of the channel and the release of its content.

The above experiment is repeated using compound IX for MscL modification and incubating the calcein filled vesicles with phosphine at pH 7.4. A significant increase in release is observed from MscL upon contacting with phosphine.

Example 5

In Vivo Delivery of Drugs from MA Labelled MscL Liposomes

Mice with an experimental induced solid tumor are injected with liposomes with azide labelled MscL (modified with compound VIII or compound IX) and containing a first radioactive labelled agent (e.g. $^{99m}Tc$). The liposome surface itself is radiolabelled with a second, different isotope. After localisation of the liposomes at the tumor site due to the EPR (enhanced permeability and retention) effect of tumors for lipids and clearance of free circulating liposomes, the labels are imaged using the signals of the two isotopes. Originally the distribution of the isotopes (content and surface of vesicle) throughout the body is identical. Hereafter Triphenylphosphine is injected into the bloodstream and the release of the first radioactive label and diffusion thereof in the body is observed. At this stage the distribution of the first and second isotopes throughout the body starts to differ. This release and diffusion of the first radioactive label is not encountered in a control experiment wherein the same liposomes (i.e. comprising first label inside vesicles and second label on surface of vesicles) are used but wherein no phosphine is injected.

Example 6

MS Investigation of Azide (VIII)-Modfied MscL Gly22Cys

The MscL labeling conditions were checked with ESI-MS. It was shown that indeed MscL was fully labeled with azide VIII. MscL subunits gave a mass of about 15,870 Da. There was no unlabeled protein, which would have a mass of 15,697 Da. Results are shown in FIG. 9.

Example 7

Preparation of the Thiol Reactive Reagent of Formula (IX), FIG. 10

Compound 15 was prepared following a published procedure disclosed in Robillard c.s. *Bioconjugate Chem.* 2008, 19, 714-718. Compound 16 was prepared following a published procedure disclosed in Kocer et al. *Angew. Chem. Int. Ed.* 2006, 45, 3126-3130. Compound 16 (132.5 mg, 0.62 mmol) and azide derivative 15 (576 mg, 1.83 mmol) were dissolved in DMF (45 mL). Triethylamine (0.5 mL) was added and the resulting bright yellow solution was stirred in the dark at RT overnight. The reaction mixture was evaporated under reduced pressure and the resulting yellow oil was purified by silica column chromatography with diethylether. Pure IX was collected as orange oil in a yield of 50% (121.5 mg, 0.313 mmol). $^1$H NMR (300 MHz, $CDCl_3$) δ 7.29 (d, 2H, J=8.3 Hz), 6.9 (d, 2H, J=8.3 Hz), 5.2 (br t, 1H), 5.1 (s, 2H), 4.4 (t, 2H, J=6.1 Hz), 4.0 (d, 2H, J=5.9 Hz), 3.4 (t, 2H, J=6.1 Hz), 3.3 (s, 3H). $^{13}$C NMR (75 MHz, $CDCl_3$) δ 170.1 (C), 156.6 (C), 140.5 (C), 133.3 (C), 130.3 (CH), 119.6 (CH), 67.0 ($CH_2$), 63.7 ($CH_2$), 51.3 ($CH_3$), 43.1 ($CH_2$), 35.2 ($CH_2$). Anal calcd for $C_{13}H_{16}N_4O_6S_2$: C 40.20, H 4.15, N 14.42, S 16.51. found: C 40.51, H 4.16, N 13.99, S 16.15. HPLC (A: 0.1% formic acid in $H_2O$; B: 0.1% formic acid in ACN; 5 to 95% B in 25 min): 14.7 min.

Example 8

Phosphine-Triggered Release from Liposomes Containing MscL Gly22Cys Modified with Azide IX MscL was fully labelled with azide IX following the protocol for azide VIII. Also, the reconstitution of VIII-labeled MscL into liposomes was performed following the protocol for VIII. The triggered liposomal release from IX-labeled MscL-containing liposomes was performed at pH 7.4, pH 6.7, pH 6.3, separately, at 37° C. Two $PPh_3$ concentrations, 5 mM and 100 µM were tested at each pH. Finally, consecutive $PPh_3$ addition was tested. The Staudinger reaction-mediated activation of IX-liposomes by $PPh_3$ in the pH range from 7.4 to 6.3 is shown in FIG. 11. The net liposomal release 3 hours after the initiation of the Staudinger reaction by addition of $PPh_3$. Net % release=% Fs−% Fc, where Fs is fluorescence of the sample to which $PPh_3$ was added and Fc is sample with no $PPh_3$ addition.

100 µM $PPh_3$ was enough to give full activity and further addition of 100 µM $PPh_3$/hr for 3 hours did not increase the activity. Full release of the liposomal content was completed within 3 hrs. The amount of liposomal release obtained after Staudinger reaction for the tested pH values was in good agreement with the expected activity from the final protein-attached amine, which was previously established in Kocer et al. *Angew. Chem. Int. Ed.* 2006, 45, 3126-3130. (FIG. 12).

The invention claimed is:

1. A composition comprising a vesicle comprising a charge sensitive channel protein or an N- and/or C-terminus fragment thereof which maintains selective passage, wherein the channel protein or fragment thereof comprises, in a side chain of an amino acid, a phosphine-reactive azide group, wherein the phosphine-reactive azide group is linked to the channel protein or fragment thereof through a sulphur and wherein the side chain of the amino acid has the structure depicted in formula (XVIII):

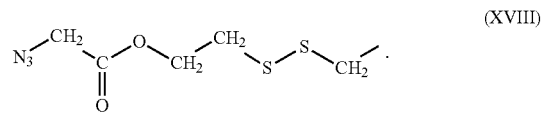

2. The composition according to claim 1, wherein the phosphine-reactive azide group is linked to a cysteine in the channel protein or fragment thereof.

3. The composition according to claim 1, wherein the channel protein is a cysteine mutant of a wild-type channel protein.

4. The composition according to claim 1, wherein the channel protein is a mechanosensitive channel of large conductance (MscL).

5. The composition according to claim 4, wherein the MscL is *E. coli* MscL comprising a Gly22Cys mutation.

6. The composition according to claim 1, further comprising a bioactive agent.

7. The composition according to claim 1, further comprising an imaging compound.

8. The composition according to claim 1, further comprising a targeting moiety.

9. The composition according to claim 1, for use as a medicament and/or imaging agent.

10. A kit comprising the composition according to claim and a phosphine.

* * * * *